United States Patent [19]

Goto et al.

[11] Patent Number: 5,144,044
[45] Date of Patent: Sep. 1, 1992

[54] NON-LINEAR OPTICAL MATERIAL AND NON-LINEAR OPTICAL DEVICE

[75] Inventors: Yoshitaka Goto, Tsukuba; Masaharu Nakayama, Tsuchiura, both of Japan

[73] Assignee: Nippon Oil and Fats Co., Ltd., Tokyo, Japan

[21] Appl. No.: 586,756

[22] Filed: Sep. 24, 1990

[30] Foreign Application Priority Data

Sep. 27, 1989 [JP] Japan .................. 1-249221

[51] Int. Cl.$^5$ .......................... C07D 333/22
[52] U.S. Cl. ...................... 549/70; 359/240; 359/321; 359/328
[58] Field of Search ............ 549/70; 350/355, 356, 350/320, 374, 370; 359/240, 321, 328

[56] References Cited

U.S. PATENT DOCUMENTS 4,892,681  1/1990  Miyata et al. .............. 252/282
4,981,641  1/1991  Miyazaki et al. ............ 350/96.3

OTHER PUBLICATIONS

N. D. Truevich et al., *Chemical Abstracts*, vol. 81, abstract No. 62911d, p. 412 (1984).

S. V. Tsukerman et al., *Chemical Abstracts*, vol. 70, abstract No. 67398z, p. 278 (1969).

Y. Goto et al., *Journal of Crystal Growth*, "Second Harmonic Generation and Crystal Growth of Substituted Thienyl Chalcone", 108, 688–698 (1991).

*Primary Examiner*—Richard L. Raymond
*Assistant Examiner*—Mark W. Russell
*Attorney, Agent, or Firm*—Malcolm B. Wittenberg

[57] ABSTRACT

A non-linear optical material consists essentially of 3-(2-thienyl)-1-(4-methylphenyl)propene-3-one represented by the formula (I)

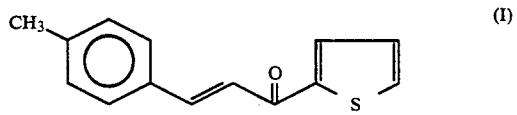

A non-linear optical device contains an organic compound disposed in a light beam. The organic compound is represented by the formula (I) and has a crystal in which a space group determined by the X-ray analytical method is $P2_1$.

7 Claims, 1 Drawing Sheet

NON-LINEAR OPTICAL MATERIAL AND NON-LINEAR OPTICAL DEVICE

BACKGROUND OF THE INVENTION

This invention relates to a non-linear optical material and a non-linear optical device.

Non-linear optical materials are the materials exhibiting so-called non-linear optical effects, in which non-linear responses result from induced polarization of electrons by the electrical field created by the light incident on the materials. These optical effects are generally due to the second and higher order terms in the following equation of $$P = \kappa^1 E + \kappa^2 E \cdot E + ^3 E \cdot E \cdot E + \cdots + \kappa^n E \cdot n$$

wherein P is polarizability of a material, E is intensity of electrical field, and $\kappa^n$ is non-linear optical susceptibility of the n'th order.

It has been known that, due to a phenomenon known as the second harmonic generation (SHG) obtained by the specific utilization of the secondary effect, an incident light is converted into a light wave corresponding to the second harmonic wave and having a frequency twice as high as the frequency of the incident light or the refractive index is changed by voltage, so that the phenomenon is very conveniently utilized for performing various optical processings including conversion of wavelengths, processing of signals and modulation of laser beams, which are extremely advantageous.

Although inorganic crystals, such as $KH_2PO_4$ (KDP), $LiNbO_3$ or $NH_4H_2PO_4$ (ADP), have hitherto been used as the non-linear optical materials, they have disadvantages that single crystals having high optical purities are very expensive, that they are so deliquescent as to be inconvenient in handling, and that the non-linear sensitivities thereof are not so high. On the other hand, since the utility of organic materials as suggested in 1983 in the symposium in the American Chemical Society, organic crystals of urea, aniline base compounds or the like were reported to be utilizable as non-linear optical materials. However, these organic compounds do not exhibit satisfactory non-linear optical effects, or the compounds which exhibit relatively high level of non-linear effect have a disadvantage that they have light absorptive terminal groups that are significantly shifted towards the long wavelength range to thus limit the wavelength range of the light waves which can be processed therethrough.

SUMMARY OF THE INVENTION

It is an object of the present invention to provide a non-linear optical material and a non-linear optical device which have high non-linear optical properties and allow phase matching and which are superior in transparency and transmission characteristics for, above all, the blue light region.

It is another object of the present invention to provide a non-linear optical device which may be utilized for wavelength conversion of various lasers.

The above and other objects of the invention will become apparent from the following description.

According to the present invention, there is provided a non-linear optical material consisting essentially of 3-(2-thienyl)-1-(4-methylphenyl)propene-3-one represented by the formula (I)

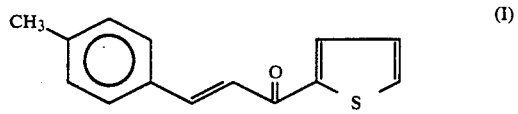

According to the present invention, there is also provided a non-linear optical device in which an organic compound is disposed in a light beam, and wherein the organic compound is 3-(2-thienyl)-1-(4-methylphenyl)-propene-3-one represented by the above formula (I), the organic compound having a crystal in which a space group determined by the X-ray analytical method is $P2_1$.

PREFERRED EMBODIMENTS OF THE INVENTION

Figure 1:
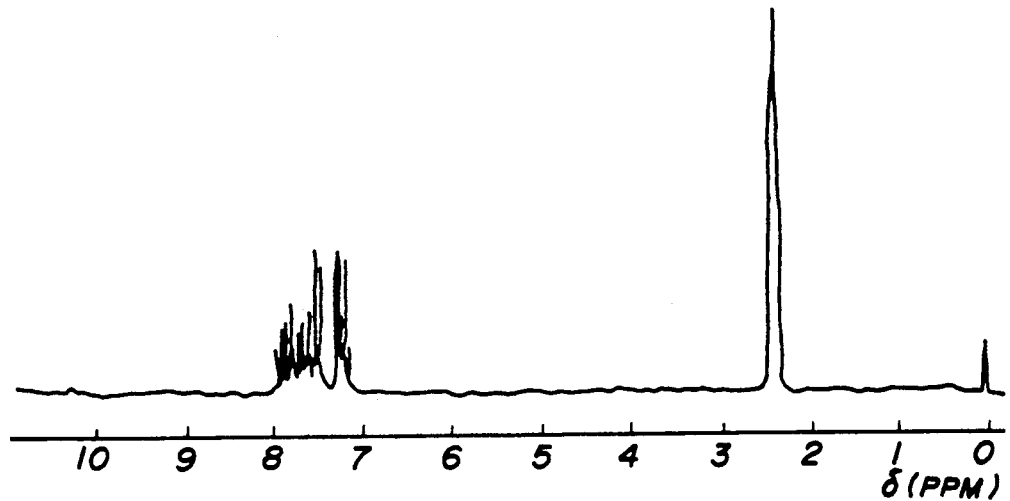
FIG. 1 is a chart showing the $^1H$-NMR spectrum of a purified product of 3-(2-thienyl)-1-(4-methylphenyl)-propene-3-one which is the non-linear optical material of the present invention.

The present invention will be explained in detail hereinbelow.

3-(2-thienyl)-1-(4-methylphenyl)propene-3-one, employed in the non-linear optical material of the present invention, is represented by the following formula (I):

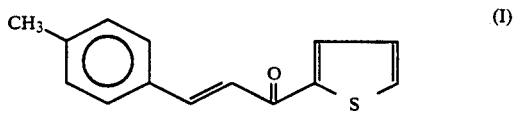

In preparing 3-(2-thienyl)-1-(4-methyl-phenyl)propene-3-one represented by the formula (I), 4-methyl benzaldehyde and 2-acetylthiophene are subjected to dehydration condensation in the presence of a basic catalyst or an acidic catalyst. Sodium hydroxide, potassium hydroxide or a variety of quaternary ammonium salts may be employed as the basic catalysts, while boron trifluoride phosphorus oxychloride or boron trifluoride etherate may be employed as the acidic catalysts. More specifically, 3-(2-thienyl)-1-(4-methylphenyl)propene-3-one of the present invention may be obtained by reacting 4-methyl benzaldehyde and 2-acetylthiophene in the temperature range of preferably 0° to 50° C. for 30 minutes to 50 hours in the presence of the above mentioned catalysts, if necessary, in suitable solvents, e.g. alcohols such as methanol or ethanol. The reaction temperature higher than 50° C. is not desirable since various secondary reactions are produced by heat, whereas the reaction temperature lower than 0° C. is also not desirable since the reaction time is prolonged with concomitant economical disadvantages.

The non-linear optical material may be prepared by purifying the non-linear optical material, that is 3-(2-thienyl)-1-(4-methylphenyl)propene-3-one, by recrystallization, either directly or with the use of, for example, suitable solvents, such as ethanol.

The non-linear optical device of the present invention is provided in which an organic compound is disposed in a light beam. The organic compound has the molecular structure of 3-(2-thienyl)-1-(4-methylphenyl)propene-3-one represented by the formula (I) and has a crystal in which a space group by the X-ray analytical method is P2₁ (Herman-Mauguin's symbol).

The above compound 3-(2-thienyl)-1-(4-methylphenyl)propene-3-one, employed in the non-linear optical device of the present invention, when seen as a molecule, exhibits an extended $\pi$-electron conjugate system and a strong tendency towards charge movement in the molecule due to the methyl group, thiophene ring and carbonyl group affixed to the benzene ring, so that hyperpolarizability may be expected. On the other hand, the crystal obtained by crystallization of 3-(2-thienyl)-1-(4-methylphenyl)propene-3-one belongs to the monoclinic system, and the space group by the X-ray analytical method is P2₁, so that it does not exhibit centrosymmetric structure but exhibits strong second order non-linear optical effects. Among the X-ray analytical methods analyses are a Debuy-Schller method and a diffractiometric method, which are well known among those engaged in the art. The space group P2₁ is one of 168 space groups, among 230 space groups, not exhibiting centrosymmetric structure. That is, the essential condition for the second order non-linear optical properties in wavelength conversion is the absence of centrosymmetric structure of the crystals.

For preparing the non-linear optical organic compound of the present invention, that is, for crystallizing 3-(2-thienyl)-1-(4-methylphenyl)propene-3-one, 3-(2-thienyl)-1-(4-methylphenyl)propene-3-one is dissolved in an organic solvent, such as benzene, toluene, xylene, methanol, ethanol, propanol, acetone, methylethylketone, chloroform, tetrahydrofuran, dioxane or hexane, to provide a saturated solution, which is then cooled gradually at a rate of 0.01 to 0.2° C. daily over 7 to 60 days or evaporating the solvent gradually over 7 to 60 days. Alternatively, as taught by Bridgeman, 3-(2-thienyl)-1-(4-methylphenyl)propene-3-one may be charged in a glass ampoule and gradually lowered therein at a rate of 0.1 to 2 mm/hr through a temperature gradient of from higher than the minimum melting point of the organic compound to lower than the maximum melting point thereof to allow crystals to grow from the gaseous phase to produce desired crystals.

The non-linear optical material of the present invention consists essentially of 3-(2-thienyl)-1-(4-methylphenyl)propene-3-one so that it exhibits extremely high non-linear optical effects as well as excellent transparency and superior transmission characteristics with respect to the region of blue light having the wavelength over 400 nm and hence may be used for a variety of optical applications. The non-linear optical device of the present invention also allows phase matching so that it may be used for wavelength conversion of various types of lasers.

EXAMPLES OF THE INVENTION

The present invention will be explained in more detail with reference to Examples and Comparative Examples.

EXAMPLE 1

1.20 g. (0.01 mol) of 4-methylbenzaldehyde and 1.26 g. (0.01 mol) of 2-acetylthiophene were charged, along with 20 ml. of ethanol, into a reaction vessel, and stirred at 25° C. while a mixed solution of 1 g. of a 40 wt. % aqueous solution of sodium hydroxide and 10 ml. of ethanol was added dropwise to the reaction system. Finally, 20 ml. of an aqueous solution of 0.5 N hydrochloric acid was added to the reaction system. After termination of the reaction, a precipitated solid was washed several times with distilled water and dried.

The so-produced crude product was recrystallized with an ethanol solvent to yield 2.05 g. of purified 3-(2-thiehyl)-1-(4-methylphenyl)propene-3-one melting at 116.3° C. at a yield of 90%. Anal. calcd. for $C_{14}H_{12}SO$: C 73.65%; H 5.30%; S 14.04%. Found: C 73.92%; H 5.09%; S 14.18%.

Figure 2:
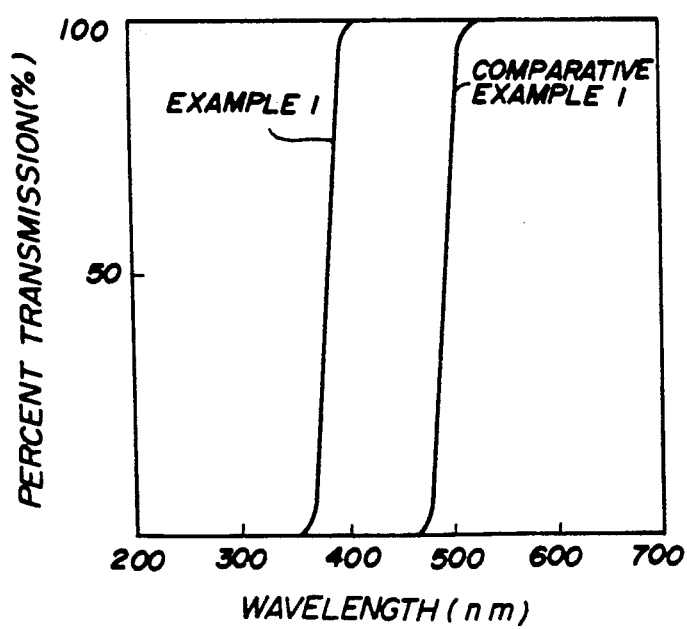
FIG. 2 is a chart showing the light absorption spectrum of a known non-linear optical material and the light absorption spectrum of a purified product of 3-(2-thienyl)-1-(4-methylphenyl)propene-3-one which is the non-linear optical material of the present invention.

The results of measurement of the ¹H-NMR spectrum and the light transmission spectrum are shown in FIGS. 1 and 2, respectively. The measurement of the second harmonic generation (SHG) of the produced compound was then performed. For measurement, the sample was granulated to the size of 50 to 150 $\mu$m in diameter and sandwiched between a pair of slide glasses. This sample was irradiated with 15 nsec pulses by an Nd⁺-YAG laser fitted with a Q-switch (wavelength : 1064 nm) to detect the second harmonics emanated from the sample. An urea sample, granulated in the similar manner, was used as a standard sample, and the ratio of the SHG strength or intensity of the sample was found with respect to the SHG strength of the urea which was set to 1. This method of measurement is well-known among those engaged in the art and described in detail in, for example, Journal of Applied Physics, vol.36, No. 8, pages 3798 to 3813, 1968.

The SHG intensity ratio of 3-(2-thienyl)-1-(4-methylphenyl)propene-3-one, as measured by the above method, was 25.

EXAMPLE 2

3-(2-thienyl)-1-(4-methylphenyl)propene-3-one prepared in Example 1 was dissolved in aceton to provide a saturated solution. The temperature of the solution was lowered over 20 days at a rate of 0.1° C. daily to produce a crystal having the size of 50×10×10 mm. It was found from X-ray analyses that the produced crystal was of the monoclinic system and the space group was P2₁. The lattice constant was: a=12.3209 Å; b=5.8782 Å; and c=17.5308 Å, whereas $\beta$=109.867°.

The refractive indices of the produced crystal along the optic elasticity axes at wavelengths of 1064 nm and 532 nm were measured by the prism method. The results are shown in Table 1.

TABLE 1

| Wavelength (nm) | Nx[1] | Ny[2] | Nz[3] |
|---|---|---|---|
| 1064 | 1.6403 | 1.6908 | 1.7659 |
| 532 | 1.7255 | 1.7353 | 1.8584 |

[1] optic elasticity x axis
[2] optic elasticity y axis
[3] optic elasticity z axis It was also found that the type I phase matching of the wavelength of the produced crystal was achieved at an angle of 28° from the axis Z in a plane including the optic elasticity x and z axes with respect to the 1064 nm laser light.

The non-linear optical properties of the produced crystal was 600 times as high as those of inorganic crystals KDP (potassium dihydrogen phosphate). The present crystal had the absorption end at 410 nm and exhibited sufficiently high transmission characteristics for the blue light. It was found from the same test conducted after the crystal was allowed to stand at 50° C. for one year that no changes were caused in the crystal appearance and properties.

Although the present invention has been described with reference to the specific examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. In a non-linear optical device in which an organic compound is disposed in a light beam, the improvement wherein the organic compound is 3-(2-thienyl)-1-(4-methylphenyl)propene-3-one represented by the formula (I)

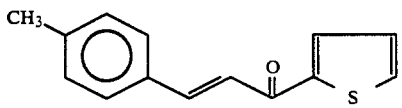

(I)

said compound having a crystal in which a space group determined by the X-ray analytical method is $P2_1$.

2. The non-linear optical device according to claim 1 wherein the crystal of said organic compound is of the monoclinic system and exhibits non-linear optical effects without exhibiting centrosymmetric structure.

3. The non-linear optical device according to claim 1 wherein said crystal of said organic compound is prepared by dissolving 3-(2-thienyl)-1-(4-methylphenyl)-propene-3-one in an organic solvent to provide a saturated solution and cooling said solution over 7 to 60 days at a rate of 0.01 to 0.2° C. daily.

4. The non-linear optical device according to claim 3, wherein said organic solvent is selected from the group consisting of benzene, toluene, xylene, methanol, ethanol, propanol, acetone, methylethylketone, chloroform, tetrahydrofuran, dioxane, hexane and mixtures thereof.

5. The non-linear optical device according to claim 1 wherein said crystal of said organic compound is prepared by dissolving 3-(2-thienyl)-1-(4-methylphenyl)-propene-3-one in an organic solvent to provide a saturated solution and evaporating said solvent over 7 to 60 days.

6. The non-linear optical device according to claim 5, wherein said organic solvent is selected from the group consisting of benzene, toluene, xylene, methanol, ethanol, propanol, acetone, methylethylketone, chloroform, tetrahydrofuran, dioxane, hexane and mixtures thereof.

7. The non-linear optical device according to claim 1 wherein said crystal of said organic compound is prepared by charging 3-(2-thienyl)-1-(4-methylphenyl)propene-3-one in a glass ampoule and lowering the crystal therein gradually at a rate of 0.1 to 2 mm/hr in a temperature gradient of from higher than a minimum melting point of said organic compound to lower than a maximum melting point of said compound to allow the crystal to grow from a gaseous phase.

* * * * *